United States Patent [19]

Blanc

[11] Patent Number: 5,635,132
[45] Date of Patent: Jun. 3, 1997

[54] PROCESS FOR DECONTAMINATION AND DETOXIFICATION APPLIED TO SANITARY ENGINEERING IN THE HOME

[76] Inventor: Michel Blanc, 44 Rue du Septentrion, 83310 Port Grimaud, France

[21] Appl. No.: 284,580

[22] PCT Filed: Feb. 5, 1993

[86] PCT No.: PCT/FR93/00121

§ 371 Date: Aug. 10, 1994

§ 102(e) Date: Aug. 10, 1994

[87] PCT Pub. No.: WO93/15774

PCT Pub. Date: Aug. 19, 1993

[30] Foreign Application Priority Data

Feb. 14, 1992 [FR] France .................... 92 01962

[51] Int. Cl.$^6$ .................... B01F 3/04; A61L 3/00
[52] U.S. Cl. .................... 422/5; 422/125; 239/60; 239/338; 239/44; 239/533.14; 261/30; 261/DIG. 65; 43/124; 43/125; 222/630; 222/644
[58] Field of Search .................... 422/5, 4, 125; 239/60, 338, 44, 533.14; 261/DIG. 65, 30; 428/905; 43/124, 125; 222/644, 630

[56] References Cited

U.S. PATENT DOCUMENTS

| | | | |
|---|---|---|---|
| 3,410,488 | 11/1968 | Sugimura | 239/55 |
| 3,993,444 | 11/1976 | Brown | 21/126 |
| 4,163,038 | 7/1979 | Nishimura et al. | 422/36 |
| 4,166,087 | 8/1979 | Cline et al. | 261/96 |
| 4,173,604 | 11/1979 | Dimacopolus | 261/30 |
| 4,308,241 | 12/1981 | DeVries | 423/210 |
| 4,627,430 | 12/1986 | Klimt | 128/200.17 |
| 4,757,812 | 7/1988 | Arborelius, Jr. | 128/200.21 |
| 4,882,873 | 11/1989 | Purnell | 43/132.1 |
| 4,951,854 | 8/1990 | Carnier et al. | 222/644 |
| 5,011,632 | 4/1991 | Yano et al. | 261/81 |
| 5,023,020 | 6/1991 | Machida et al. | 261/18.1 |
| 5,029,729 | 7/1991 | Madsen et al. | 221/1 |
| 5,030,253 | 7/1991 | Tokuhiro et al. | 55/89 |
| 5,063,706 | 11/1991 | Aki et al. | 43/125 |
| 5,302,359 | 4/1994 | Nowatzki | 422/306 |
| 5,335,446 | 8/1994 | Shigetoyo | 43/125 |
| 5,370,317 | 12/1994 | Weston | 239/533.14 |

FOREIGN PATENT DOCUMENTS

| | | |
|---|---|---|
| 391934 | 12/1990 | Austria . |
| 0036339 | 10/1981 | European Pat. Off. . |
| 0231084 | 8/1987 | European Pat. Off. . |
| 9012600 | 1/1990 | WIPO . |

OTHER PUBLICATIONS

Lucien Dautresande *Microaerosols* (New York Academic Press, 1962) 1–23.
Anthony J. Hickey, *Pharmaceutical Inhalation Aerosol Technology* (New York: Marcel Dekker, Inc., 1992) 129–155.
William C. Hinds, *Aerosol Technology* (New York: Wiley, 1982).
Lucien Dautresande, *Microaerosols* (New York: Academic Press, 1962).
Stewart W. Clarke and Demetri Pavia, *Aerosols and the Lung* (London: Butterworths,1984) 78–79.
Folke Mofen, et al, Aerosols in Medicine: Principles, *Diagnosis and Therapy* (Amsterdam: Elsevier, 1985) 71–72.
George M. Hidy, *Aerosols an Industrial and Environmental Science* (Orlando: Academic Press, Inc., 1984) 126–132.
Penaud, A. et al. 'Methods Of Destroying House Dust Pyroglypid Mites', Clinical Allergy, vol. 5, no. 1, Mar. 1975, pp. 109–114.

*Primary Examiner*—Nina Bhat
*Attorney, Agent, or Firm*—Ladas & Parry

[57] ABSTRACT

A process for decontamination and detoxification of a room wherein an atomizer is used to diffuse a product containing essential oils as a mist. The outer openings of the room to be decontaminated and detoxified are closed and the product is diffused as a true aerosol from the center of the room. After the diffusion is stopped, the mist is allowed to decontaminate and detoxify room and the room is then aired.

7 Claims, No Drawings

PROCESS FOR DECONTAMINATION AND DETOXIFICATION APPLIED TO SANITARY ENGINEERING IN THE HOME

BACKGROUND OF THE INVENTION

1. Field of the Invention

The present invention relates to a process for decontamination and detoxification applied to sanitary engineering in the home.

The technical sector of the invention and its application are in the domain of hygiene and sanitary engineering in the home, for domestic purposes.

2. Description off the Related Art

The terms ecology and environment have become commonplace especially concerning nature, but their definition should also include the study of the home: in fact, it may be noted that the word "ecology" comes etymologically from the Greek word "oikos", meaning house and "logos", science. Moreover, this home is contaminated by all sorts of so-called live particles which are responsible for a specific pathology, named "domestic lung" in the publication and conference made by Messrs. Michel BLANC and Bruno BLAIVE at the Versailles "Forum Contaminé Expert" on 13th, 14th and 15th Sep. 1989; this term has been defined as grouping together the pathological states due to the multiple aggressors of pollution inside homes, provoked both by the components of the house dust produced by animals, plants, bacteria, insects, pollens, mould, viruses, etc., and which create biocontamination, and by the particles issuing from the combustion of tobacco and products coming from the outside due to industrial combustion and to automobile traffic.

There is addition and interference between these very diverse particles in the sense of added, pathological, deleterious effects, involving, for example particles from combustion and biocontamination. This also is the case for the particles of tobacco and mould, namely nicotine and acarids.

It should be noted that the contamination of the inside atmosphere also depends on the contamination of the outside atmosphere, that it is bound thereto and that it is always greater.

This contamination is different from biocontamination, as it is physical (rare gases, electro-magnetic elements, etc.) and chemical (industrial combustion, $SO_2$, $NO_2$, etc.). It further interferes in the configuration of the particles of the domestic ambient air, which the human being inhales at a rate of 800 millions of particles per day, of which the major part is absorbed by the organism.

Their quality and quantity are such that, normally, they are not noxious, sometimes even the contrary. However, when they fix toxic and/or contaminated additives, when they are concentrated in a large quantity (which is the case in confined, poorly ventilated dwellings), then their inherent toxicity is apparent.

These particles are in particular generated by the ejections of acarids, themselves raised in a composite, mutant culture medium.

Acarids make a veritable compost of house dust, in the same way as those of the forest make humus. They find in the dwelling a biotope which is always propitious, coming from numerous factors already cited, and in particular the conditions of temperature and humidity favourable to their development, all the more so in modern dwellings, in particular in the bathrooms and ventilation systems.

There is a veritable permanent recycling by the acarids of the particles thus generated which are then concentrated by them; it is admitted that the major allergen of "domestic lung" is contained in the ejections, "specks", of acarids. The semi-quantitative colorimetric dosage of nitrogenous metabolite guanine is a veritable index of contamination of house dust, whilst being specific of its presence. This test is thus found positive in dust in carpentry workshops and bakeries, in henhouse dust, and in house dust: there is thus a good correlation between this test and the clinical manifestations associated with allergies to house dust and acarids.

Now, the constant threat of a respiratory pathology associated with the inhalation of particles is progressing in a disquieting manner, whereas curative treatments have never been as widely employed and as efficient. This paradoxal failure may be explained by ignorance, by a deterioration of elementary hygiene in the dwelling, and by the insufficient means for purifying the ambient air, whereas everything leads one to think that the origin of the pollution is essentially, at the start, outside.

Living conditions in a reduced, overpopulated, confined dwelling and the obvious regression of domestic hygiene made one believe in the appearance of so-called "civilization" diseases.

In fact, this pulmonary pathology is associated with the ambient air of the dwelling.

Architecture, energy savings, pollution associated with combustion, and in particular passive smoking, the presence of domestic animals, the change in morals, the conditions of heating, producing condensations, the presence of bathrooms which are poorly or not ventilated, generating humidity, the systems of ventilation, etc., all transform the biotope of the living being which depends thereon and which is indissociable therefrom.

Studies and research have been developed to propose processes and products either, on the one hand, to treat the persons themselves in order to fight and treat their allergies with suitable medicines, although this is not the approach of the present invention; or to destroy the source of these allergies, which is the fundamental rule in the study of allergies. For example, the acarids which have dominated for more than ten years the discussions and preoccupations of therapists by the importance of the reactions that they generate.

In this context, mention may be made of the publication by Messrs. PENAUD, NOURRIT, AUTRAN, TIMON-DAVID, JAQUET FRANCILLON and CHARPIN on "Methods of destroying house pyroglyphid mites" in the review Clinical Allergy of 1975, Vol. 5, pages 109 to 114; and of the conferences of Messrs. BLANC and BOUTIN on the 14th, 15th and 16th of Nov. 1989 in Brussels on "The destruction of acarids and biodecontamination of the domestic environment".

These publications and conferences, and many others may be cited, were essentially based on the convincing results of the clinical action of acaricidal products used as atmosphere aerosols with the aid of an "atomizer"; these products, of which one in particular has been tested with success within this framework, and which has been used in particular application in a hospital environment for more than forty years in the domain of disinfection of bed-linen, are based on essential oils and have been known for a long time, not only for their anti-acarid effects, but also their anti-fungal and anti-bacterial effects.

The action of these products is therefore proved in these particular cases of application, allowing a deposit of particles of products on the surfaces, with a view essentially to destroying the acarids. The idea was then to use these acaricidal products electively on mattresses, for example, with the aid of aerosol sprays, which in fact do not produce a veritable aerosol, but instead produce a spray with particles between 20 and 100 microns; this spray propulsion presents major drawbacks, such as the problems associated with the ozone, their price, etc., but is used by the manufacturers and distributors of these products.

Thus, the clinical contributions of the modification of the particular environment of the asthmatic allergic to acarids were observed and studied with a certain success.

However, despite these interesting, promising results, (and the development of sanitary engineering in the dwelling, including the choice of materials, the types of ventilation, and the orientation of the rooms to reduce the causes of pollution and poor hygiene) the respiratory pathology associated with the inhalation of the particles in the dwelling increases because of, the noxiousness of the particles being concentrated by the acarids, which are the principal cause of allergies, as has been described hereinabove.

The problem raised is that of being able to ensure a better and more efficient decontamination of the dwelling than the present processes mentioned above, which are oriented toward the treatment of the surfaces and the destruction of the acarids considered to be the principal allergens.

The inventor has in fact observed, against the generally accepted ideas and principles mentioned above, that, in certain dwellings where there are large quantities of acarids, the persons living therein are not allergic to said acarids and are not indisposed; he has therefore ascertained that there may be healthy acarids and that even they are necessary for the balance of nature, and that to destroy them was doubtlessly not the ultimate solution, particularly because as, in other dwellings where few acarids were noted, the occupants showed signs of allergy.

It has therefore been considered that, rather than treating the surfaces and acarids directly, it would be better to treat the source of pollution, the dust itself.

SUMMARY OF THE INVENTION

One solution to the problem raised, within the scope of the present invention, is that of preparing each room of said dwelling so that all the elements of furniture which compose it are exposed to the ambient air of said room; closing all the outer openings thereof; diffusing said product as a true aerosol from the centre of the room in particles of 0.2 to 2 microns maximum for a sufficient period of time; thus treating, with the mist emitted and composed of said particles of product, all the volume of air of the room in question and all the exposed surfaces; then stopping the diffusion of said product, keeping the room in question closed for a duration sufficient for the product to act, before airing said room; cleaning the surfaces with a simple, damp wipe.

Said product used is preferably a rich formulation of ten constituents and which contains in particular essential oils such as essential oil of lilac, essential oil of lemon, essential oil of citronella, aromatic essences such as terpineot for a percentage of about 20% grouping together all the essential oils and aromatic essences, and phenolic derivatives of natural origin, such as benzoic acid, salol and thymol for a minimum of 4%, and antiseptic products such as triclosan for about 0.2% of the total composition, all these components being in solution in an aliphatic solvent likewise of natural origin, for the remaining 70 to 76%.

DESCRIPTION OF THE PREFERRED EMBODIMENT

In a preferred embodiment, said product is diffused as an aerosol for a determined period of time, defined as a function of the volume of said room and of the flow-rate diffused by the atomizer, such that the quantity of products in suspension in said room volume is at least one ml/m$^3$, which represents a time of operation of about 15 minutes for an average room. The time during which the room must then remain closed is some hours, in principle 3 hours.

The result is a novel process and a novel application of products within the framework of the decontamination and detoxification of a dwelling.

This process according to the invention in fact responds to the problem raised, as it attacks the toxic dust directly before the acarids concentrate it and reject it. In fact, the process according to the invention makes it possible, thanks to the product used and its aerolization by gaseous diffusion in fine particles, to obtain true aerosols which directly burst the bacteria which may be located on said dust; it may also be considered that the product thus diffused has an ionizing and precipitating action in this form and behaves as veritable "antiparticles", destroying bacteria, fixed on a carrier particle (reference Henry's law on bactericide in gaseous phase).

In this way, the atmosphere itself, but also, of course, the surfaces which are the only ones treated at the present time, are detoxified efficiently by employing the products in question.

On this subject, in addition to the explanations given above, it may be defined what the term "toxic" means according to the dictionary: "is said of a noxious substance for a living organ"; and detoxification or detoxication is the destruction and reduction of the toxicity by neutralization of the toxic power of certain bodies by their combination with other substances in vitro and in vivo by the action of certain organs.

The process according to the invention therefore consists in the simultaneous use of an atmosphere aerolizer apparatus generating fine submicronic particles with a mixture of essential oils recognized as having an action of neutralization, decontamination and detoxification of the particles in suspension in the ambient air of the whole of a contaminated dwelling, and also present on the horizontal and vertical surfaces of this dwelling.

According to the references and publications mentioned above on the analysis of the numerous phenomena of different natures, which combine to render toxic the particles of the ambient air inhaled, the inventor has considered that, if a means makes it possible to decontaminate the particles by modifying their nature, to purify the ambient air by lowering the quantity of particles by agglutination and precipitation, and to destroy the biological particles such as the mould generating endotoxin, this process would then be welcome; this is all the more interesting in an increasingly serious epidemiological situation of respiratory diseases associated with the toxicity of the dust inhaled, although this manner of approaching the problem and not of treating it at the level of the acarids or the allergic patient himself, has up to the present time been set aside and not retained by the professional circles concerned.

This approach on the aspect of the toxicity of the dust which may thus be eliminated thanks to the process of the present invention is therefore novel and all the more inventive as it goes against the principles used up to the present time.

In order to obtain the desired effect of the process of the present invention, the apparatus used is a generator of a mist of fine particles, hence the name of atomizer: it is an atmosphere aerosolizer which will diffuse in the whole dwelling, room by room, from the cellar to the attic, submicronic aerosols of the appropriate mixture.

In order to obtain the desired particle dimension of 0.2 to 2 microns maximum, the operational principle of this apparatus preferably resides in the use of the centrifugal force furnished by a plate rotating at high speed to fragment a liquid which has been sucked in parallel by a suction cone.

The particles then emitted by the generator are true aerosols and the fineness of the particles obtained makes dry aerosols thereof, which do not stain the surfaces on which they are deposited and differentiate them singularly from the aerosols emitted by sprays by diffusion, which are not true aerosols, but particles included between 20 and 100 microns.

The product used itself is preferably an original rich formulation of ten constituents, of which the principle active part is constituted by essential oils, which are products known since at least 1928, and which give said product acaricidal, anti-fungal, and anti-bacterial properties, which are confirmed by the work made by the users of this type of product for numerous years.

This product presents no toxicity for man and is perfectly tolerated by plants and animals. It is a product for use in the presence of humans. Furthermore, it is nonflammable and does not stain at all when it is diffused in the form of true aerosols.

From the physical standpoint, this product has a power of agglutination and of precipitation of the particles in suspension in the ambient air and of the particles deposited on the surrounding surfaces. This property is enhanced in decontaminations of acarids in dwellings wherein the mattresses in particular are exposed to the product chosen, as these are the privileged places where the particles generated by the acarids are concentrated, and wherein surfaces that are difficult to reach such as the inside of cupboards and wardrobes are also exposed to the chosen product, for these surfaces are where the acarids, mould and bacteria also thrive. However, it is solely by a direct action of the decontaminating and acaricidal aerosols on these surfaces that the products considered for that are used up to the present time.

The process and the particular application of the product within the framework of the present invention makes it possible not only to conserve these same qualities of products as indicated hereinabove, but in addition to be able to treat the house dust directly in order to detoxify it at the origin even before it can be deposited on the surfaces and then concentrated by the acarids; in fact, the particles are constantly in suspension in the ambient air and are therefore accessible only by other particles in suspension having a high power of diffusion, as ensured by an atomizer of the type according to the invention. The acarids may then continue to develop in the house without concentrating toxicity, and therefore without influence on the occupants: they will therefore no longer be a cause of allergy.

The process according to the invention is to be repeated at a sufficient interval of time to maintain this quality of hygiene of the ambient air at a level of nontoxicity and to avoid having to treat the persons living in the dwelling curatively and medically.

It is in this respect that the present invention lies in the domain of domestic sanitary engineering in the home and is not concerned with anything medical. The present invention is not a therapy applied to a patient, but is solely a means for maintaining a dwelling in a satisfactory state of salubrity. It contributes a measure of hygiene, an indispensable complement to the therapeutical medical instructions.

What is claimed is:

1. A process for decontamination and detoxification of at least one room, wherein each said room is prepared so that all objects in said room are accessible, the process comprising:
    a) providing an oil-based composition consisting essentially of essential oils, aromatic essences, phenolic derivatives of natural origin, and antiseptic products in solution in an aliphatic solvent, the essential oils including at least essential oil of lilac, essential oil of lemon, and essential oil of citronella;
    b) closing all outer openings of the room and exposing all objects in the room to the ambient air of the room, wherein particles are suspended in the ambient air;
    c) diffusing from an apparatus comprising an atomizer, a suction cone and a plate the composition of step a) as a true aerosol until the concentration of the aerosol in the room is at least 1 ml/m$^3$, the aerosol having aerosol particles obtained by using centrifugal force furnished by the plate rotating at high speed to fragment said composition which has been sucked in parallel by the suction cone, the aerosol particles having a size of 0.2 to 2 microns;
    d) stopping the diffusion of said composition;
    e) allowing the aerosol to decontaminate and detoxify the particles suspended in the ambient air; and
    f) airing the room.

2. A process as claimed in claim 1, wherein the aerosol consists essentially of aerosol particles having a maximum size of 0.2 to 2 microns.

3. A process as claimed in claim 1, wherein the aromatic essence is terpineol, the antiseptic product is triclosan, and the phenolic derivatives are selected from the group consisting of benzoic acid, salol, and thymol.

4. A process as claimed in claim 3 wherein the aresol particles are diffused from the center of the room.

5. A process as claimed in claim 2, wherein the aromatic essence is terpineol, the antiseptic product is triclosan, and the phenolic derivatives are selected from the group consisting of benzoic acid, salol, and thymol.

6. A process a as claimed in claim 1 wherein the aresol particles are diffused from the center of the room.

7. A process as claimed in claim 2 wherein the aresol particles are diffused from the center of the room.

* * * * *